United States Patent
Ritter

(10) Patent No.: US 12,350,413 B2
(45) Date of Patent: Jul. 8, 2025

(54) FLUID HANDLING SYSTEMS AND METHODS

(71) Applicant: B. BRAUN MEDICAL INC., Bethlehem, PA (US)

(72) Inventor: Kai-Uwe Ritter, Bethlehem, PA (US)

(73) Assignee: B. BRAUN MEDICAL INC., Bethlehem, PA (US)

( * ) Notice: Subject to any disclaimer, the term of this patent is extended or adjusted under 35 U.S.C. 154(b) by 0 days.

(21) Appl. No.: 17/846,185

(22) Filed: Jun. 22, 2022

(65) Prior Publication Data

US 2023/0414849 A1    Dec. 28, 2023

(51) Int. Cl.
 *A61M 1/16*    (2006.01)
 *A61M 1/36*    (2006.01)
 *A61M 39/22*   (2006.01)
 *A61M 39/28*   (2006.01)

(52) U.S. Cl.
 CPC ........ *A61M 1/1621* (2014.02); *A61M 1/3649* (2014.02); *A61M 39/223* (2013.01); *A61M 39/28* (2013.01)

(58) Field of Classification Search
 CPC .............. A61M 1/1601; A61M 1/3643; A61M 1/3647; A61M 1/1621; A61M 1/3649; A61M 39/223; A61M 39/28
 See application file for complete search history.

(56) References Cited

U.S. PATENT DOCUMENTS

| | | | |
|---|---|---|---|
| 4,540,399 A | * | 9/1985 | Litzie .................. A61M 1/3647 604/122 |
| 7,135,008 B2 | | 11/2006 | O'Mahony et al. |
| 7,713,226 B2 | | 5/2010 | Ash |
| 8,409,127 B2 | | 4/2013 | Gronau et al. |
| 8,523,799 B2 | | 9/2013 | Biesel et al. |
| 8,721,884 B2 | | 5/2014 | Wilt et al. |
| 8,980,094 B2 | | 3/2015 | Fischer |
| 9,072,843 B2 | | 7/2015 | Kelly et al. |
| 9,579,440 B2 | | 2/2017 | Hogard et al. |
| 9,592,332 B2 | | 3/2017 | Gunther et al. |
| 9,616,471 B2 | | 4/2017 | Haecker et al. |

(Continued)

FOREIGN PATENT DOCUMENTS

| | | | | |
|---|---|---|---|---|
| CN | 114404703 A | * | 4/2022 | ............ A61M 1/16 |
| WO | 2021067247 A1 | | 4/2021 | |
| WO | 2021150460 A1 | | 7/2021 | |

*Primary Examiner* — Guy K Townsend
*Assistant Examiner* — Peter Daniel Smith
(74) *Attorney, Agent, or Firm* — CM Law PLLC; Stephen J. Weed

(57) ABSTRACT

A dialysis system with post dialysis aseptic blood return including a fluid source, a dialyzer, a pump, a venous line, an arterial line, a bridge line coupled between the venous line and the arterial line, and a fluid source line coupled between the fluid source and a fluid port of the arterial line downstream for the bridge line. Aseptic blood return after dialysis is performed by blocking the arterial line between the bridge line and the fluid port, unblocking the bridge line, unblocking the fluid source line, and operating the pump in a forward direction to produce fluid flow from the fluid source, through the dialyzer, and through the bridge line to force venous blood in the venous line toward the patient venous access and arterial blood in the arterial line toward the patient arterial access.

19 Claims, 11 Drawing Sheets

(56) References Cited

U.S. PATENT DOCUMENTS

| | | |
|---|---|---|
| 9,913,939 B2 | 3/2018 | Bachmann et al. |
| 10,245,369 B2 | 4/2019 | Kelly et al. |
| 10,653,826 B2 | 5/2020 | Kelly et al. |
| 2003/0138348 A1* | 7/2003 | Bell ................... A61M 1/367 604/4.01 |
| 2009/0101576 A1* | 4/2009 | Rohde ................ A61M 1/3643 96/204 |
| 2014/0326646 A1* | 11/2014 | Strohhoefer ........ A61M 1/1617 210/85 |
| 2016/0136346 A1* | 5/2016 | Cho ................... A61M 1/1601 210/136 |
| 2019/0001042 A1 | 1/2019 | Buckberry |
| 2020/0405941 A1 | 12/2020 | Ikuma |
| 2021/0001033 A1* | 1/2021 | Fulkerson ........... A61M 1/3606 |
| 2021/0023291 A1 | 1/2021 | Brugger et al. |
| 2021/0170090 A1 | 6/2021 | Yuds et al. |
| 2021/0252204 A1 | 8/2021 | Hogard et al. |
| 2023/0144031 A1* | 5/2023 | Roemmelt .......... A61M 1/3643 604/6.11 |
| 2023/0270923 A1* | 8/2023 | Chiaki ................ A61M 1/165 604/5.01 |

\* cited by examiner

FLUID HANDLING SYSTEMS AND METHODS

TECHNICAL FIELD

The present subject matter relates to dialysis system and, more particularly, to systems and methods for handling fluids in dialysis systems.

BACKGROUND

Dialysis systems are used to treat blood to remove impurities. During dialysis treatment with a dialysis system, blood is withdrawn from a patient, passed through a dialyzer that removes the impurities, and returned to the patient. Tubing connects the patient to the dialyzer. At the end of the dialysis treatment aseptic blood remains in the tubing and the dialyzer.

Blood return from the tubing and dialyzer, and disconnection of the patient after a dialysis treatment involves the risk of contamination and infection for the patient and caregiver. Conventionally, returning blood from the tubing and dialyzer to the patient involves disconnecting the arterial line patient access from the patient while still filled with blood and connecting the arterial line patient access to a saline source. The saline is then pushed through the tubing and dialyzer, which forces the blood back to the patient through the venous line patient access. Disconnecting the arterial line patient access from the patient while the arterial line is filled with blood creates open ends that are exposed to contamination and infections risks.

SUMMARY

In some aspects, the techniques described herein relate to a dialysis system including a fluid source, a dialyzer having a venous port and an arterial port, a pump configured to engage tubing lines, a venous line fluidly coupled to the venous port of the dialyzer, an arterial line engaging the pump and fluidly coupled to the arterial port of the dialyzer on a first engagement side of the pump, a bridge line coupled between the venous line and the arterial line on a second engagement side of the pump, and a fluid source line coupled between the fluid source and a fluid port of the arterial line on the second engagement side of the pump between the bridge line and the pump.

In some aspects, the techniques described herein relate to a method for aseptic blood return after dialysis with a dialysis system that includes configuring the dialysis system for aseptic blood return to a patient, the patient coupled to a patient venous connection end of the venous line and a patient arterial connection end of the arterial line, by blocking the arterial line between the bridge line and the fluid port, unblocking the bridge line, and unblocking the fluid source line; and operating a pump of the dialysis system in a forward direction to produce fluid flow from the fluid source, through the dialyzer, and through the bridge line to force venous blood in the venous line toward the patient venous access and blood in the arterial line toward the patient arterial access.

BRIEF DESCRIPTION OF THE DRAWINGS

Features of the various implementations disclosed will be readily understood from the following detailed description, in which reference is made to the appended drawing figures. A reference numeral is used with each element in the description and throughout the several views of the drawing. When a plurality of similar elements is present, a single reference numeral may be assigned to like elements, with an added letter referring to a specific element. When referring to such elements generally or to a non-specific element, the letter may be omitted.

The various elements shown in the figures are not drawn to scale unless otherwise indicated. The dimensions of the various elements may be enlarged or reduced in the interest of clarity. The several figures depict one or more implementations and are presented by way of example only and should not be construed as limiting. Included in the drawing are the following figures.

DETAILED DESCRIPTION

In the following detailed description, numerous specific details are set forth by way of examples to provide a thorough understanding of the relevant teachings. However, it should be apparent to those skilled in the art that the present teachings may be practiced without such details. In other instances, well known methods, procedures, components, and circuitry have been described at a relatively high-level, without detail, to avoid unnecessarily obscuring aspects of the present teachings.

Figure 1:
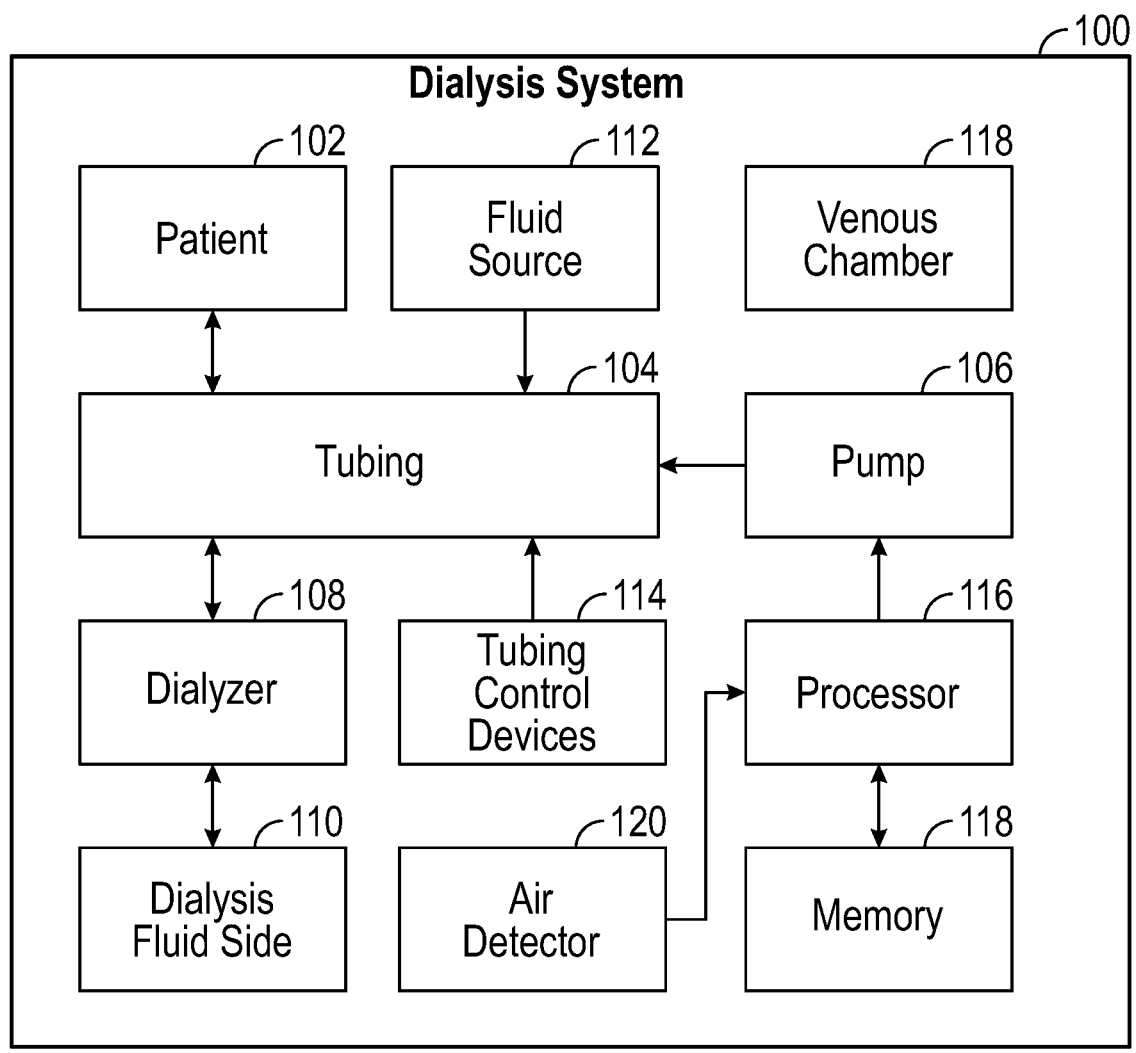
FIG. 1 is a block diagram of a dialysis system for providing dialysis to a patient.

FIG. 1 is a block diagram of a dialysis system 100 for providing dialysis treatments to a patient 102. The patient 102 is connected to the dialysis system 100 via tubing 104 (described below with reference to FIGS. 2A and 2B). A pump 106 engages the tubing 104 to control the flow of blood from the patient 102 through the tubing 104, through a dialyzer 108, and back through the tubing 104 to the patient 102. The blood flows through the dialyzer 108 adjacent dialysis fluid from a dialysis fluid side 110, which removes impurities from the blood.

A fluid source 112 provides fluid for use in priming the tubing 104 prior to a dialysis treatment and for returning aseptic blood in the tubing 104 back to the patient 102 after the dialysis treatment. In an example, the fluid is saline. The fluid may be stored in a 1-liter bag connected to the tubing 104.

Tubing control devices 114 control available pathways for fluid flow through the tubing 104. In one example, the tubing control devices 114 are clamps. The clamps may include a manually operated clamp(s) such as manually operated pinch clamp, a controllable clamp(s) such as a selectively controllable electronic clamp, or a combination thereof. In another example, one or more of the tubing control devices are valves such as a three-way valve, which may be manually or electrically operated.

A processor 116 is coupled to memory 118 and to the pump 106. Additionally, the processor 116 may be electrically connected to selectively controllable clamps and valves. The memory 118 may be a non-transitory computer readable storage medium storing program instructions for controlling the pump 106 and configuring the dialysis system 100 tubing control devices 114. The non-transitory computer readable storage medium may be random access memory (RAM), read only memory (ROM), other type of memory capable of storing program instructions, or a combination thereof.

Figure 2A:
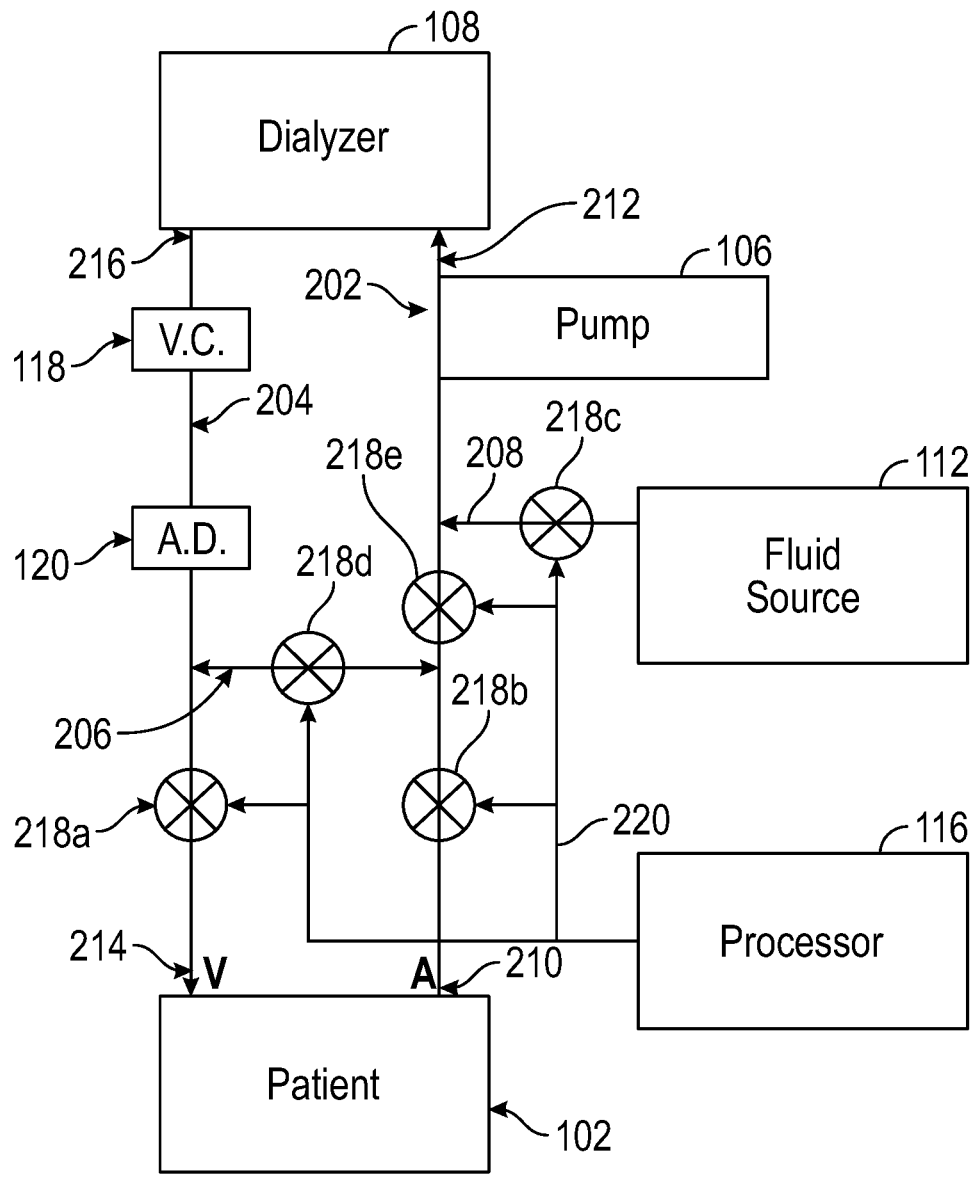
FIG. 2A is a block diagram illustrating tubing and tubing control devices for use in the dialysis system of FIG. 1 where the tubing control devices are clamps.

A venous chamber 118 such as a drip chamber is positioned in the tubing 104 (i.e., in the venous line 204; FIG. 2A) to separate air from the blood flowing through the tubing 104 so that air doesn't reach the patient. An air detector 120 is positioned in the tubing 104 downstream of the venous chamber 118. The air detector 120 is coupled to the processor 116 and is used by the processor 116 to detect the presence of air remaining in the tubing 104 downstream of the venous chamber 118. If the amount of air in the tubing 104 is above a threshold level that could potentially hurt the patient 102, the processor 116 stops the pump 106 (and optionally closes one or more valves) to prevent the air from the reaching the patient 102. The air detector 120 may be a bubble detector, a blood level detector, or other device capable of detecting the presence/absence of air.

FIG. 2A is a block diagram illustrating the tubing 104 and tubing control devices 114 (FIG. 1) in further detail where the tubing control devices 114 are clamps 218. The illustrated tubing 104 includes an arterial line 202, a venous line 204, a bridge line 206, and a fluid source line 208. The arterial line 202 extends between an arterial patient connection port 210 and an arterial port 212 of the dialyzer 108. The venous line 204 extends between a venous patient connection port 214 and a venous port 216 of the dialyzer 108. As used herein, the term arterial is used to refer to connections and lines that pass blood from the patient 102 to the dialyzer 108 during a dialysis therapy and the term venous is used to refer to connections and line that pass blood from the dialyzer 108 back to the patient 102 during the dialysis therapy.

The arterial line 202 is in engagement with the pump 106, with a first portion of the arterial line 202 on a first engagement side of the pump 106 fluidly coupled to the arterial port 212 and a second portion of the arterial line 202 on a second engagement side of the pump 106 fluidly coupled to the patient 102. The bridge line 206 is fluidly coupled between the venous line 204 and the second portion of the arterial line 202 on the second engagement side of the pump 106. In one example, a single air detector 120 is positioned in the venous line 204 and the bridge line 206 is fluidly coupled to the venous line 204 downstream of the air detector 120 as illustrated in FIG. 2A. This arrangement enables the use of a single air detector 120 to detect air in fluid flowing back to the patient 102 through the venous line 204 and through the arterial line 202 via the bridge line 206 during blood return (which is described in further detail below). In another example, a venous line air detector 120 is positioned in the venous line 204 and an arterial line air detector (not shown) is positioned in the arterial line 202 with the bridge line 206 fluidly coupled to the venous line 204 upstream of the venous line air detector 120 and fluidly coupled to the arterial line 202 downstream of the arterial line air detector. Other arrangements of the bridge line 206 and the air detector(s) 120 will be understood by one of skill in the art from the description herein.

The bridge line has an interior that defines a volume. In one example of bridge line 206, the diameter of an interior cross-section is between 3.6 mm and 4.0 mm, the length is between 80 mm and 100 mm, and the volume is between about 0.3 ml and 0.7 ml. The fluid source line 208 is fluidly coupled between the fluid source 112 and a fluid port of the arterial line 202 on the second engagement side of the pump 106 between the bridge line 206 and the pump 106. In an example, the portion of the venous line 204 downstream of the bridge line 206 connection to the venous line 204 and the portion of the arterial line 202 upstream of the bridge line 206 connection to the venous line 202 are approximately equal in length (e.g., each between 1.5 meters and 2.0 meters).

A first clamp 218a is positioned in the venous line 204 between the bridge line 206 and the patient 102 (e.g., adjacent the patient 102) to selectively block/unblock fluid flow. A second clamp 218b is positioned in the arterial line 202 between the bridge line 206 and the patient 102 (e.g., adjacent the patient 102) to selectively block/unblock fluid flow. A third clamp 218c is positioned in the fluid source line 208 to selectively block/unblock fluid flow. A fourth clamp 218d is positioned in the bridge line 206 to selectively block/unblock fluid flow. A fifth clamp 218e is positioned in the arterial line 202 between the bridge line 206 and the fluid source line 208 to selectively block/unblock fluid flow. In one example, the clamps 218a-e are manually actuated to block and unblock fluid flow. In another example, one or more of the clamps 218a-e are electrically actuated via control signals on control signal paths 220 extending between the processor 116 and respective clamps 218a-e.

Figure 2B:
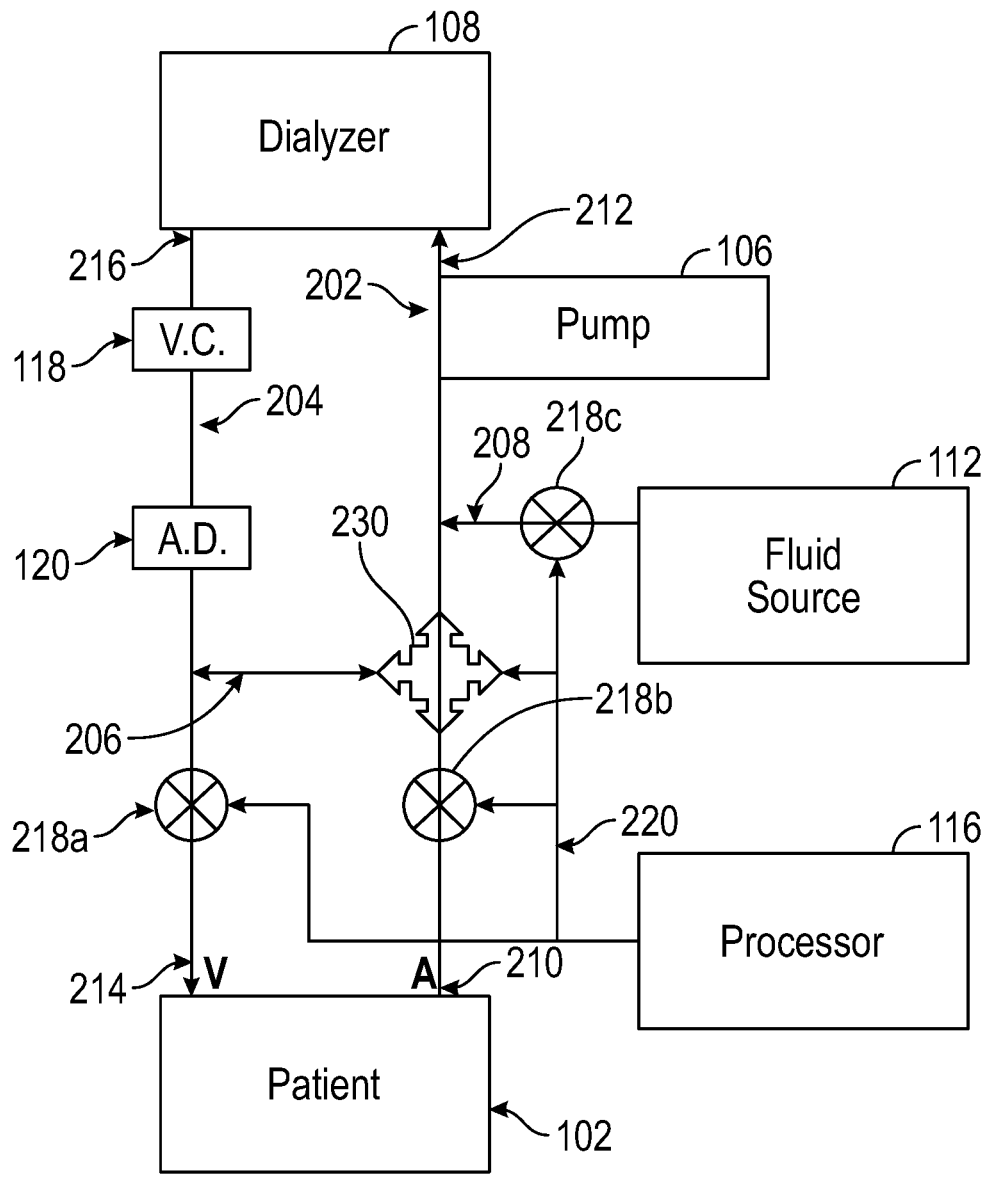
FIG. 2B is a block diagram illustrating tubing and tubing control devices for use in the dialysis system of FIG. 1 where the tubing control devices are a combination of clamps and a valve.

FIG. 2B is a block diagram illustrating the tubing 104 and tubing control devices 114 (FIG. 1) in further detail where the tubing control devices are a combination of clamps and a valve. In FIG. 2B, the fourth clamp 218d and the fifth clamp 218e of FIG. 2A are replaced by a three-way valve 230 (e.g., a stop cock valve). In one example, the three-way valve 230 is manually actuated to direct fluid flow. In another example, the three-way valve 230 is electrically actuated via control signals on control signal paths 220 extending between the processor 116 and the three-way valve 230.

FIGS. 3A-3D illustrate different configurations of the three-way valve 230. The three-way valve 230 includes a first port coupled to the bridge line 206 on the arterial line side, a second port coupled to an upstream portion of the arterial line 202, and a third port coupled to a downstream portion of the arterial line 202. As used herein, the term upstream refers to a direction from which fluid is received during a dialysis therapy and the term downstream is used to refer to a direction to which a fluid is passed during the dialysis therapy regardless of the actual flow direction of fluid (e.g., flow direction may be in a different direction during a priming phase than during the dialysis therapy).

Figure 3A:
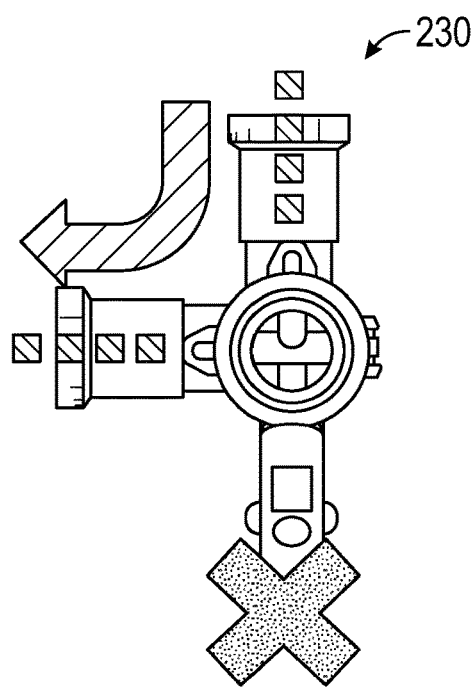
FIG. 3A is an illustration of a valve configured to prime the bridge line.

FIG. 3A is an illustration of the three-way valve 230 configured for use to prime the bridge line 206. In this configuration, fluid flow is blocked at the second port, and the first and third ports are connected to allow fluid from the fluid source line 208 to flow through the arterial line 202 and into the bridge line 206.

Figure 3B:
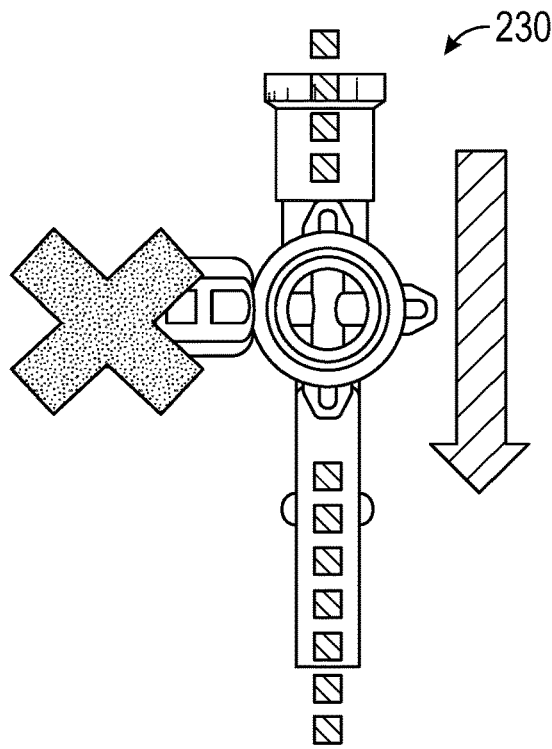
FIG. 3B is an illustration of the valve of FIG. 3A configured to prime the arterial line and the venous line.
Figure 3C:
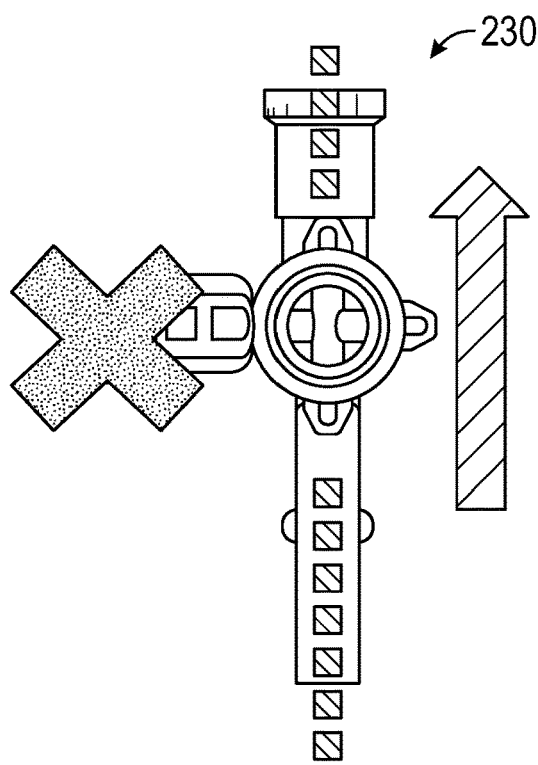
FIG. 3C is an illustration of the valve of FIG. 3A configured for use during therapy.

FIGS. 3B and 3C are illustrations of the three-way valve 230 of FIG. 3A configured to prime the arterial line and the venous line (FIG. 3B) and for use during therapy (FIG. 3C). In these configurations, the first port is blocked, and the second and third ports are connected to allow fluid flow through the arterial line 202.

Figure 3D:
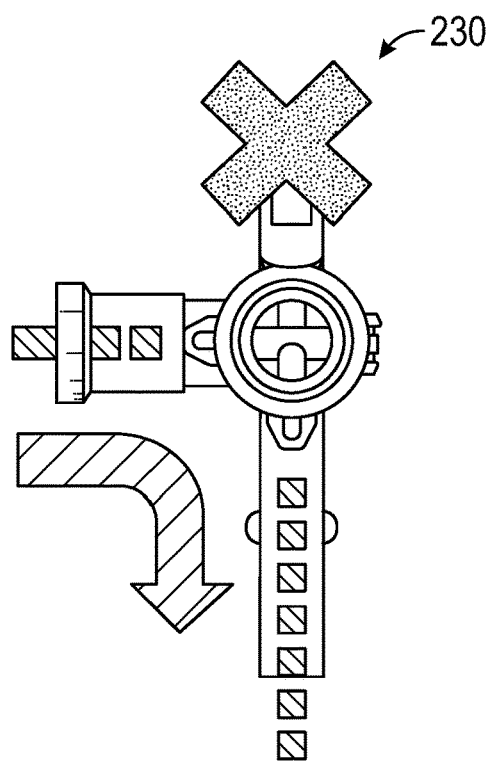
FIG. 3D is an illustration of the valve of FIG. 3A configured to return aseptic blood to the patient.

FIG. 3D is an illustration of the three-way valve 230 of FIG. 3A configured to return aseptic blood to the patient. In this configuration, fluid flow is blocked at the third port, and the first and second ports are connected to allow fluid from the bridge line 206 to flow into the arterial line 202 upstream toward the patient.

Figure 4:
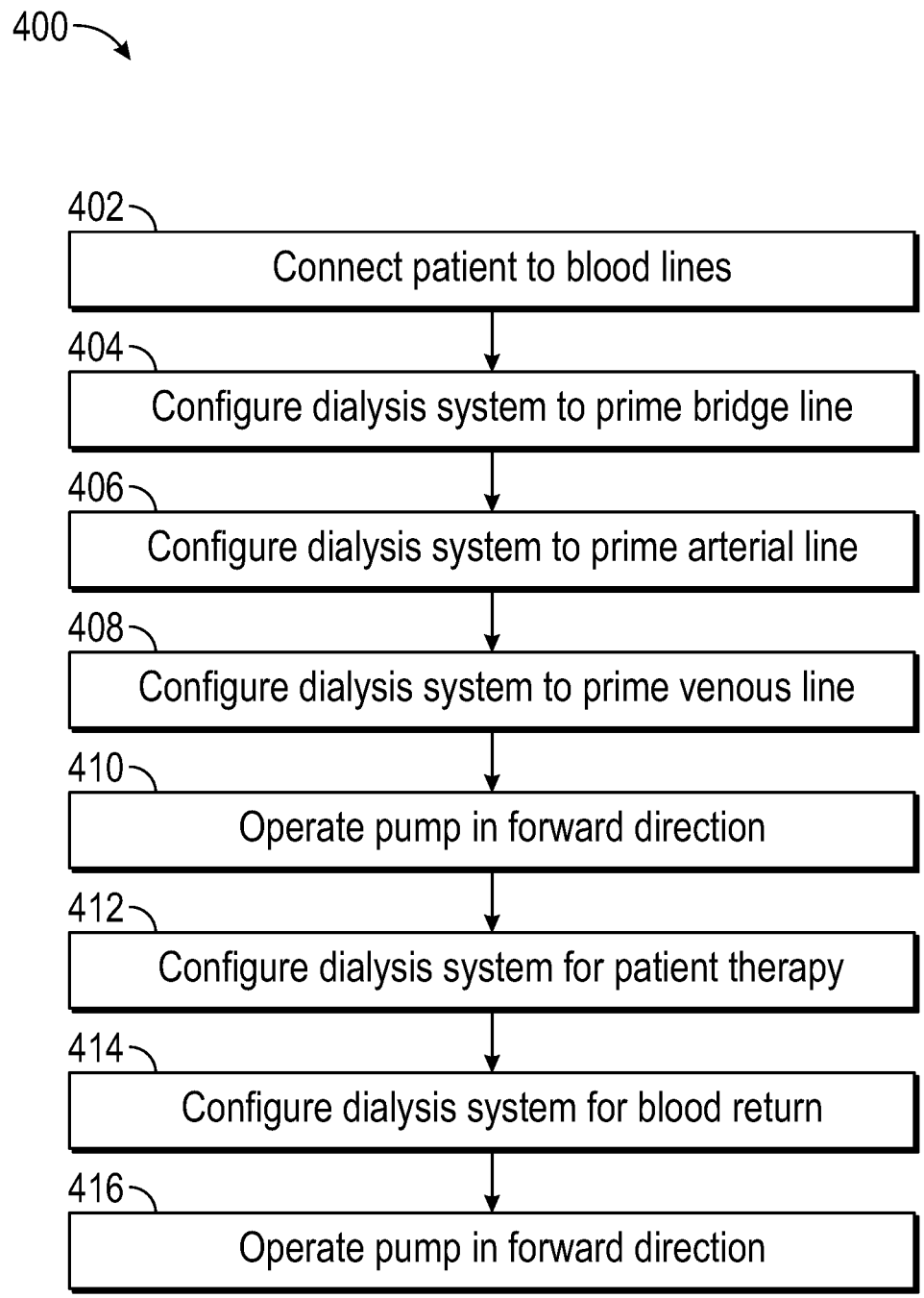
FIG. 4 is a flowchart 400 of example steps of configuring a dialysis system.

FIG. 4 is a flowchart 400 of example steps of configuring a dialysis system. Although the steps are described with reference to dialysis system 100, other suitable systems in which one or more steps of the flowchart 400 can be practiced will be understood by one of skill in the art from the description herein. Additionally, it is contemplated that one or more of the steps shown in FIG. 4, and described herein, may be omitted, performed simultaneously or in series, performed in an order other than illustrated and described, or performed in conjunction with additional steps.

At block 402, a care giver connects the patient to the blood lines. In an example, the patient access of the arterial line 202 is connected to a vein of the patient and the patient access of the venous line 204 is connected to the same vein of the patient downstream of the arterial line patent access.

Figure 5A:
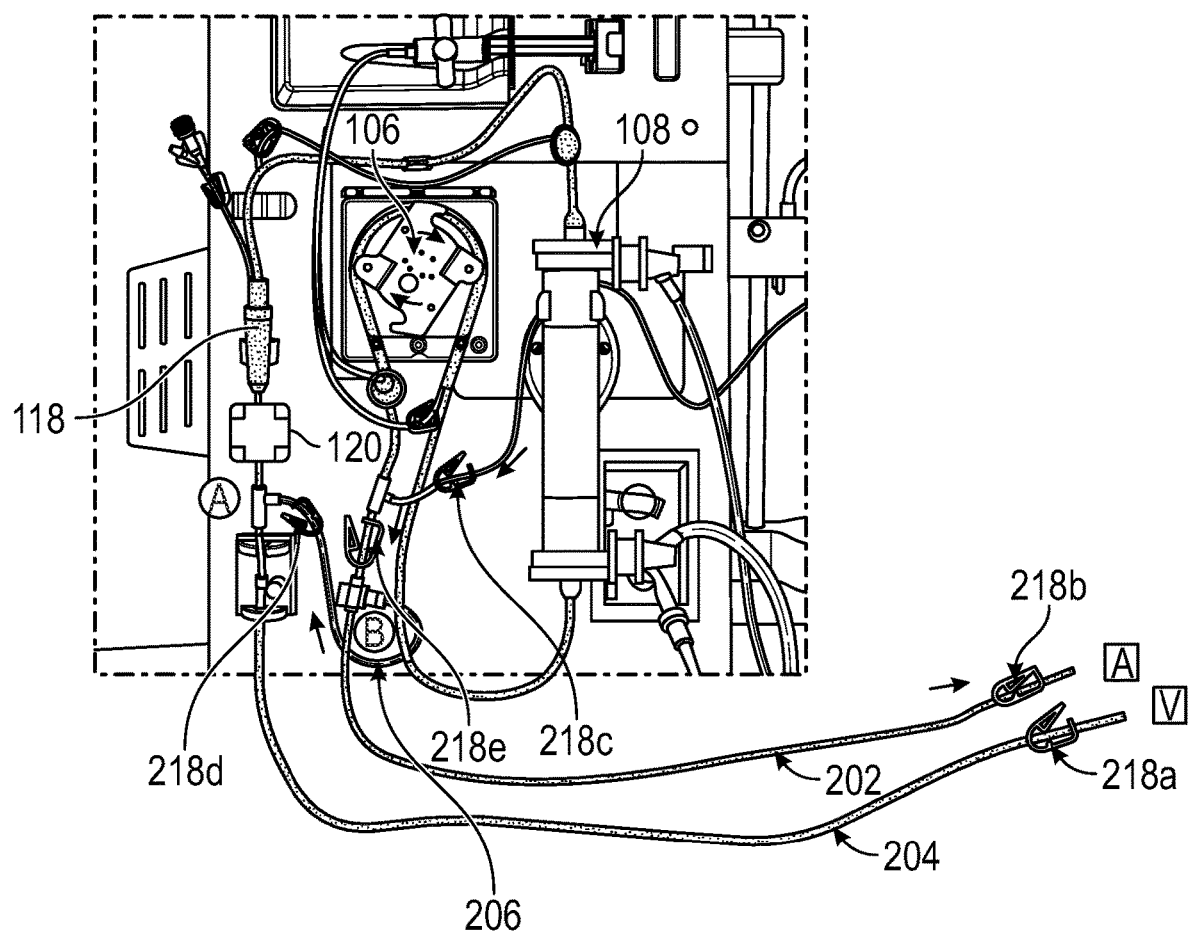
FIGS. 5A, 5B, 5C, 5D, and 5E are illustrations of a dialysis system in various configurations using clamps.

At block 404, the dialysis system 100 is configured to prime the bridge line 206. FIG. 5A depicts the dialysis system 100 configured to prime the bridge line using clamps 218a-e in accordance with one example. To configure the dialysis system to prime the bridge line 206 in accordance with this example, the first clamp 218a is open to allow fluid to flow toward the venous patient access, the second clamp 218b is closed to prevent flow toward the arterial patient access, the third clamp 218c is open to allow fluid (e.g., saline) to flow from the fluid source line 208 into the arterial line 202, the fourth clamp 218d is open to allow fluid flow through the bridge line 206, and the fifth clamp 218e is open to allow fluid flow from the fluid source line 208, through the arterial line 202, and into the bridge line 206 to prime the bridge line 206. To prime the bridge line 206, it is not necessary to run the pump 106.

Figure 6:
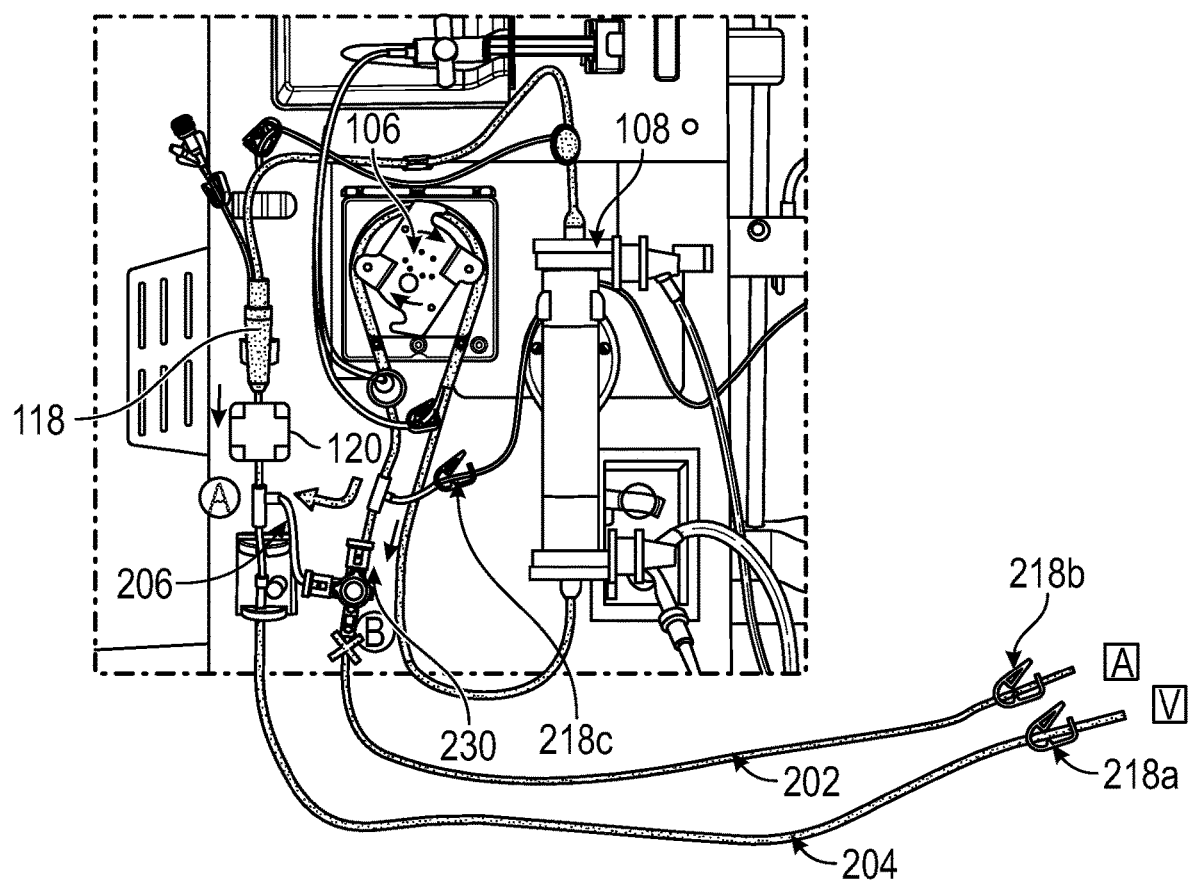
FIG. 6 is an illustration of a dialysis system configured for priming a bridge line using clamps and a three-way valve.

In another example, the fourth clamp 218d and the fifth clamp 218e, are replaced by a three-way valve 230 such as depicted in FIG. 6. In accordance with this example, the first, second, and third clamps 218a-c are configured in the same manner and the three-way valve 230 is configured to allow fluid flow from a downstream portion of the arterial line 202 into the bridge line 206 and block fluid flow from an upstream portion of the arterial line 202.

In one example, the clamps 218a-e and the three-way valve 230 are manually actuated to configure the dialysis system 100 to prime the bridge line 206. In another example, one or more of the clamps 218a-e and the three-way valve are selectively controlled by the processor 116.

Figure 5B:
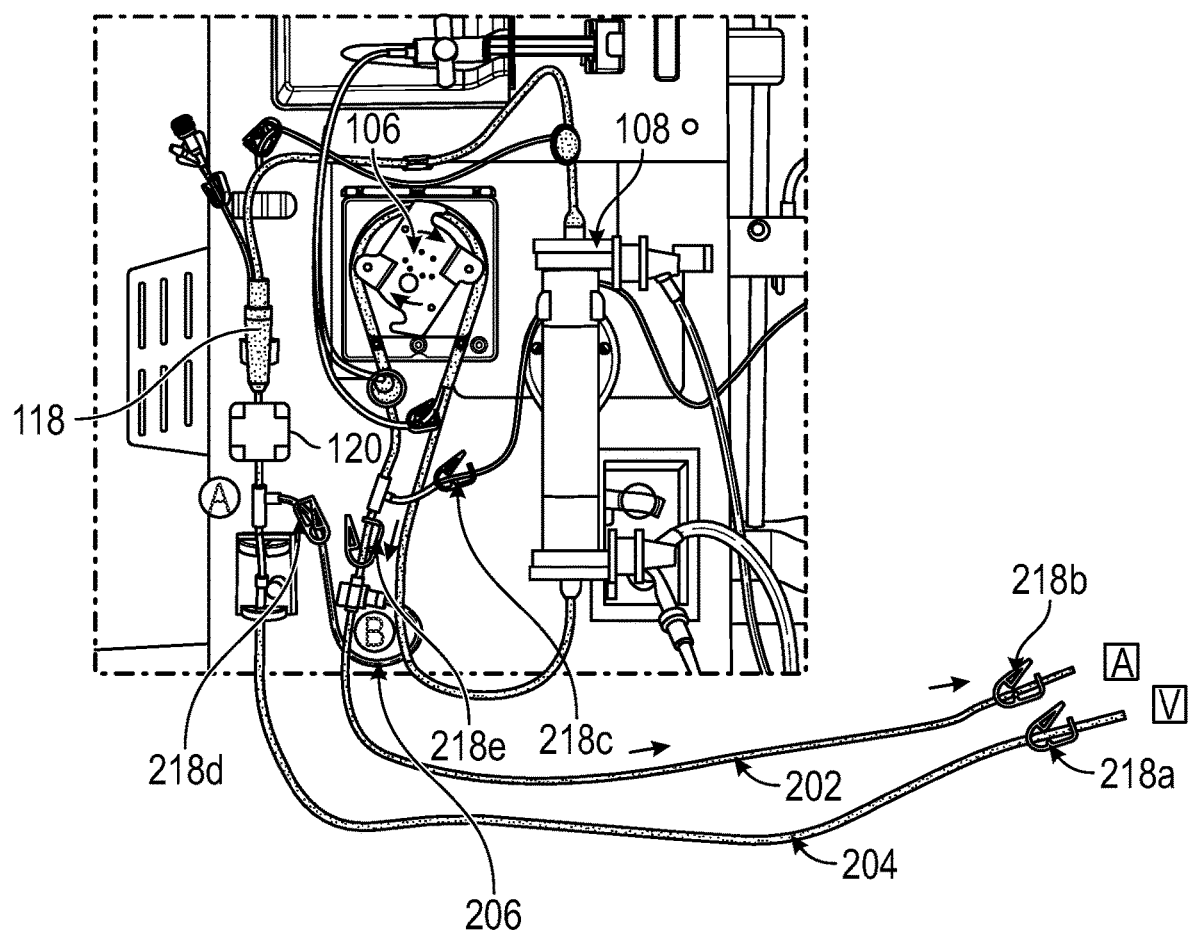

At block 406, the dialysis system 100 is configured to prime the arterial line 202. FIG. 5B depicts the dialysis system 100 configured to prime the arterial line 202 using clamps 218a-e in accordance with one example. To configure the dialysis system to prime the arterial line 202 in accordance with this example, the first clamp 218a is open to allow fluid to flow toward the venous patient access, the second clamp 218b is open to allow fluid flow toward the arterial patient access, the third clamp 218c is open to allow fluid (e.g., saline) to flow from the fluid source line 208 into the arterial line 202, the fourth clamp 218d is closed to prevent fluid flow through the bridge line 206, and the fifth clamp 218e is open to allow fluid flow from the fluid source line 208, through the arterial line 202, and toward the patient arterial access to prime the arterial line 202. To prime the arterial line 202, it is not necessary to run the pump 106.

In another example, the fourth clamp 218d and the fifth clamp 218e, are replaced by a three-way valve 230 such as depicted in FIG. 6. In accordance with this example, the first, second, and third clamps 218a-c are configured in the same manner and the three-way valve 230 is configured to allow fluid flow from a downstream portion of the arterial line 202 toward the patient arterial access and block fluid flow through the bridge line 206.

In one example, the clamps 218a-e and the three-way valve 230 are manually actuated to configure the dialysis system 100 to prime the arterial line 202. In another example, one or more of the clamps 218a-e and the three-way valve are selectively controlled by the processor 116.

Figure 5C:
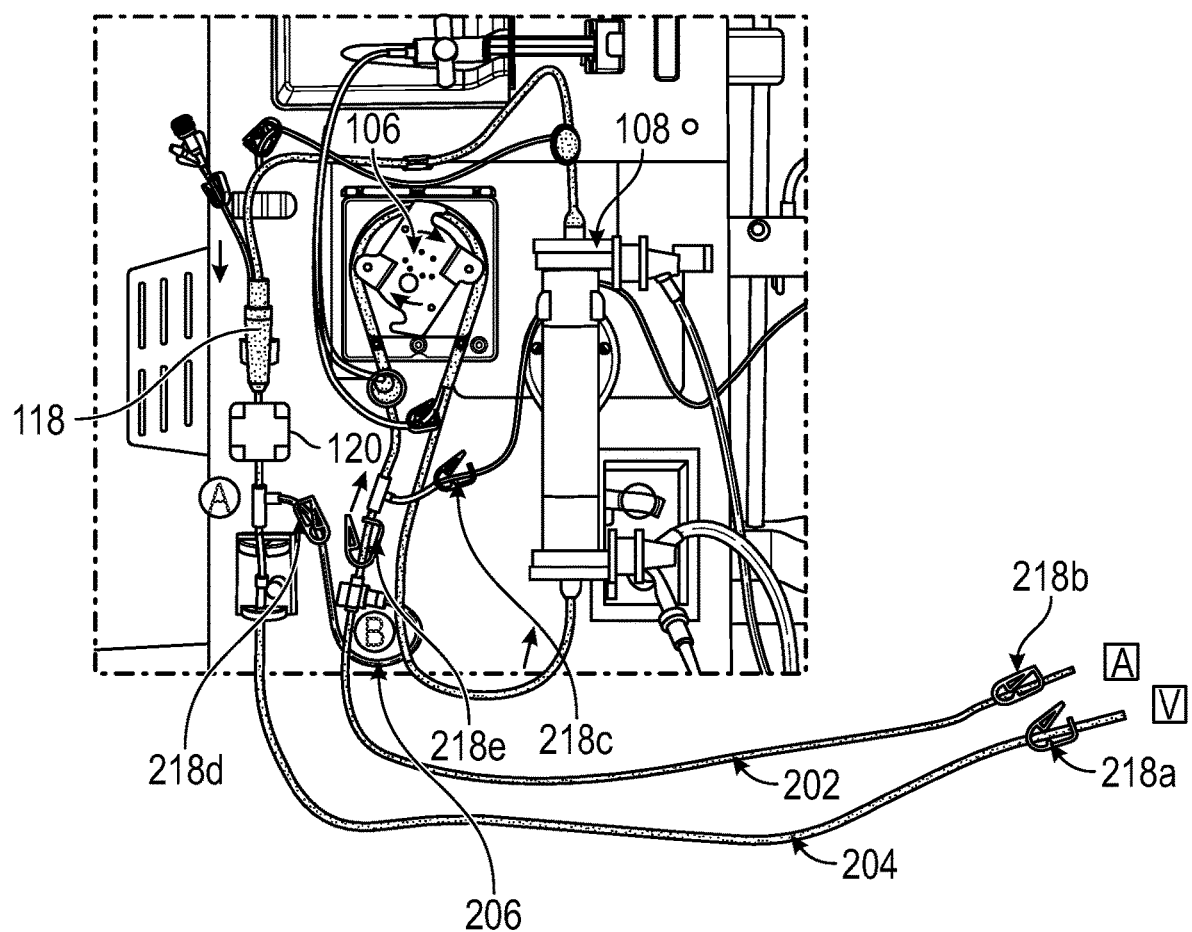

At block 408, the dialysis system 100 is configured to prime the venous line 204. FIG. 5C depicts the dialysis system 100 configured to prime the venous line 204 using clamps 218a-e in accordance with one example. To configure the dialysis system to prime the venous line 204 in accordance with this example, the first clamp 218a is open to allow fluid to flow toward the venous patient access, the second clamp 218b is closed to prevent fluid flow toward the arterial patient access, the third clamp 218c is open to allow fluid (e.g., saline) to flow from the fluid source line 208 into the arterial line 202, the fourth clamp 218d is closed to prevent fluid flow through the bridge line 206, and the fifth clamp 218e is open. To prime the venous line 204, the pump 106 is operated in a forward direction to push fluid through the dialyzer 108 and into the venous line 204 toward the venous patient access.

In another example, the fourth clamp 218d and the fifth clamp 218e, are replaced by a three-way valve 230 such as depicted in FIG. 6. In accordance with this example, the first, second, and third clamps 218a-c are configured in the same manner and the three-way valve 230 is configured to allow fluid flow from an upstream portion of the arterial line 202 toward a downstream portion of the arterial line 202 access and to block fluid flow through the bridge line 206.

In one example, the clamps 218a-e and the three-way valve 230 are manually actuated to configure the dialysis system 100 to prime the venous line 204. In another example, one or more of the clamps 218a-e and the three-way valve are selectively controlled by the processor 116.

At block 410, the pump 106 is operated in a forward direction. Operating the pump 106 in a forward direction while the dialysis system 100 is configured to prime the venous line 204 pushes fluid in the arterial line through the dialyzer and into the venous line 204. Operating the pump 106 in the forward direction is also used to provide a dialysis therapy when the dialysis system is configured to provide the dialysis therapy (see block 412).

Figure 5D:
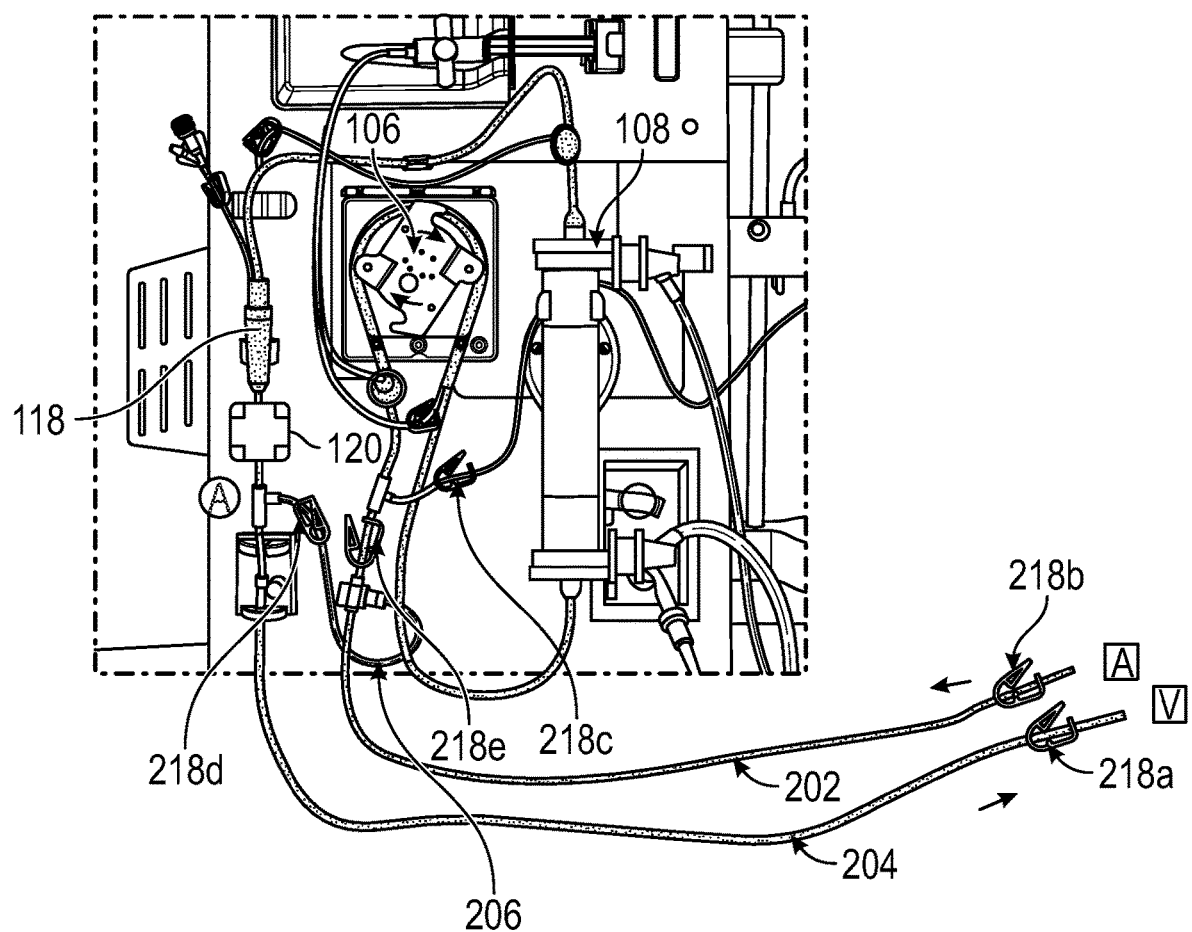

At block 412, the dialysis system 100 is configured to provide dialysis therapy. FIG. 5D depicts the dialysis system 100 configured to provide dialysis therapy using clamps 218a-e in accordance with one example. To configure the dialysis system 100 to provide dialysis therapy in accordance with this example, the first clamp 218a is open to allow fluid to flow toward the venous patient access from the dialyzer 108, the second clamp 218b is open to allow fluid flow from the arterial patient access, the third clamp 218c is closed to prevent fluid (e.g., saline) to flow from the fluid source line 208 into the arterial line 202, the fourth clamp 218d is closed to prevent fluid flow through the bridge line 206, and the fifth clamp 218e is open to allow fluid flow from the patient access to dialyzer 108. To provide dialysis therapy, the pump 106 is operated in a forward direction to push fluid from the arterial line 202 through the dialyzer 108 and into the venous line 204 toward the venous patient access.

In another example, the fourth clamp 218d and the fifth clamp 218e, are replaced by a three-way valve 230 such as depicted in FIG. 6. In accordance with this example, the first, second, and third clamps 218a-c are configured in the same manner and the three-way valve 230 is configured to allow fluid flow from an upstream portion of the arterial line 202 toward a downstream portion of the arterial line 202 and to block fluid flow through the bridge line 206.

In one example, the clamps 218a-e and the three-way valve 230 are manually actuated to configure the dialysis system 100 to provide the patient therapy. In another example, one or more of the clamps 218a-e and the three-way valve are selectively controlled by the processor 116.

Figure 5E:
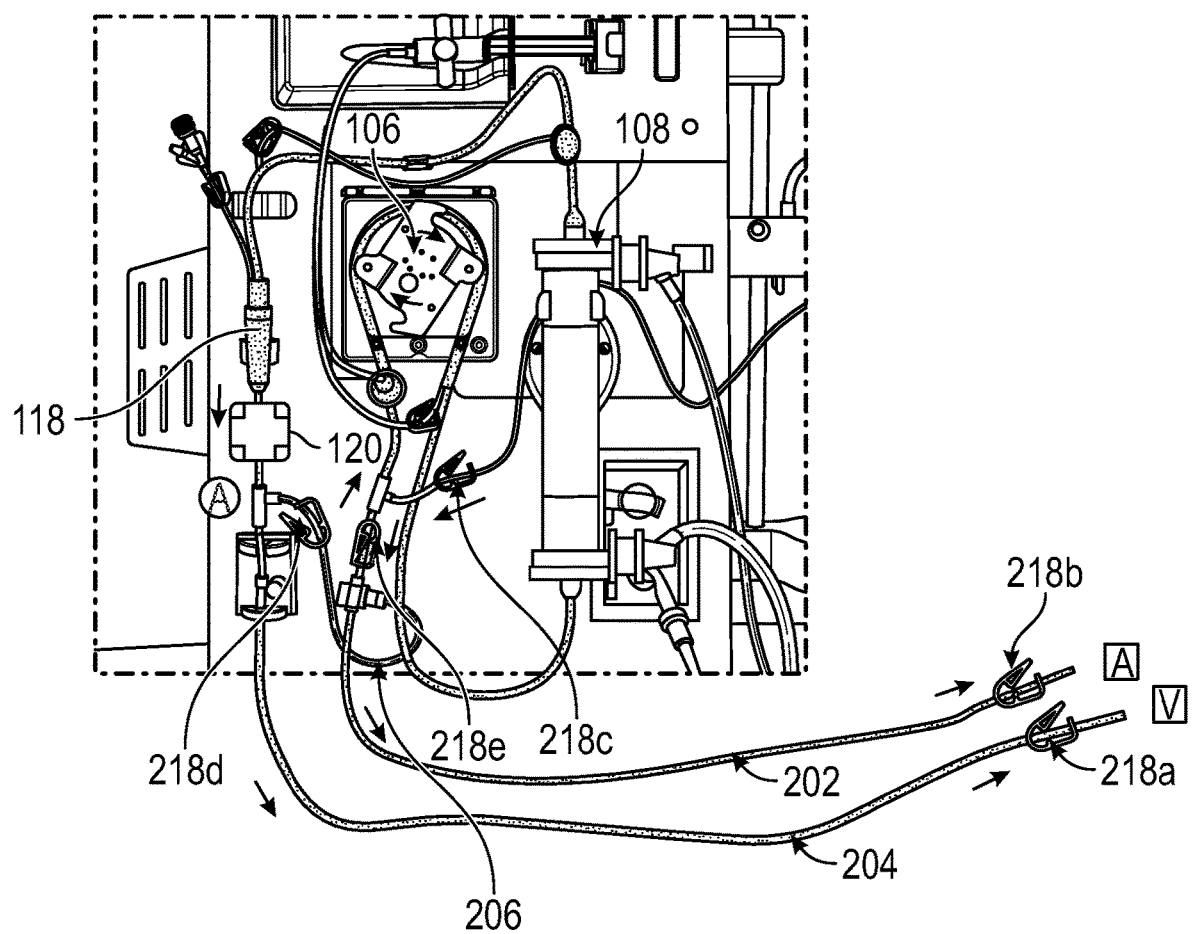

At block 414, the dialysis system 100 is configured to return aseptic blood to the patient after the dialysis therapy. FIG. 5E depicts the dialysis system 100 configured to return aseptic blood after the dialysis therapy using clamps 218a-e in accordance with one example. To configure the dialysis system 100 to return aseptic blood in accordance with this example, the first clamp 218a is open to allow fluid to flow toward the venous patient access from the dialyzer 108, the second clamp 218b is open to allow fluid flow toward the arterial patient access, the third clamp 218c is open to allow fluid (e.g., saline) to flow from the fluid source line 208 into the arterial line 202, and the fourth clamp 218d is open to allow fluid flow through the bridge line 206. The fifth clamp 218e is closed to prevent fluid flow from the fluid source line 208 directly to the patient arterial access. Rather, the fluid is pushed through a downstream portion of the arterial line 202, through the dialyzer 108, and into the venous line 204 where a portion of the fluid flows toward the venous patient access to return blood in the venous line 204 to the patient and another portion of the fluid flows through the bridge line 206 into an upstream portion of the arterial line 202 toward the arterial patient access to return blood in an upstream portion of the arterial line to the patient. To return blood to the patient, the pump 106 is operated in a forward direction to push fluid from the arterial line 202 through the dialyzer 108 and into the venous line 204 toward the venous patient access and into the bridge and through the upstream portion of the arterial line 202 toward the arterial patient access.

In one blood return example, the processor 116 via an air detector 120 positioned in the venous line 204 upstream of the bridge line 206 actively monitors fluid flowing through the venous line 204 toward the bridge line 206 and stops the pump 106 if an unacceptable level of air is detected in the venous line 204. This prevents air from reaching the patient through the venous line 204 or through the arterial 202 via the bridge line 206. In another blood return example, the processor 116 via a venous air detector 120 positioned in the venous line 204 downstream of the bridge line 206 and an arterial air detector (not shown) positioned in the venous line 204 upstream of the bridge line 206 actively monitors fluid flowing through the venous line 204 and through the arterial line 202, respectively, and stops the pump 106 if an unacceptable level of air is detected in either line. This arrangement also prevents air from reaching the patient through the venous line 204 or through the arterial 202 via the bridge line 206.

In another example, the fourth clamp 218d and the fifth clamp 218e, are replaced by a three-way valve 230 such as depicted in FIG. 6. In accordance with this example, the first, second, and third clamps 218a-c are configured in the same manner and the three-way valve 230 is configured to allow fluid flow through the bridge line 206 to an upstream portion of the arterial line 202 and to block fluid flow toward the downstream portion of the arterial line 202 line.

In one example, the clamps 218a-e and the three-way valve 230 are manually actuated to configure the dialysis system 100 to return aseptic blood. In another example, one or more of the clamps 218a-e and the three-way valve are selectively controlled by the processor 116.

At block 416, the pump 106 is operated in a forward direction. Operating the pump 106 in a forward direction while the dialysis system 100 is configured to return aseptic blood pushes fluid in the arterial line through the dialyzer and into the venous line 204.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as separately claimed subject matter.

While the foregoing has described what are the best mode and other examples, it is understood that various modifications may be made therein and that the subject matter disclosed herein may be implemented in various forms and examples, and that they may be applied in numerous applications, only some of which have been described herein. It is intended by the following claims to claim all modifications and variations that fall within the true scope of the present concepts.

What is claimed is:

1. A dialysis system comprising:
a fluid source;
a dialyzer having a venous port and an arterial port;
a pump configured to engage tubing lines;

a venous line fluidly coupled to the venous port of the dialyzer, an arterial line engaging the pump and fluidly coupled to the arterial port of the dialyzer on a first engagement side of the pump;
a bridge line coupled between the venous line and the arterial line on a second engagement side of the pump;
a fluid source line coupled between the fluid source and a fluid port of the arterial line on the second engagement side of the pump between the bridge line and the pump;
a memory configured to store program instructions; and
a processor coupled to the memory, the processor configured to process the program instructions to:
configure the dialysis system for aseptic blood return to a patient, when the patient is coupled to a patient venous access and a patient arterial access of the arterial line, by blocking the arterial line between the bridge line and the fluid port, unblocking the bridge line, and unblocking the fluid source line; and
operate the pump in a forward direction while the dialysis system is configured for aseptic blood return to produce fluid flow from the fluid source, through the dialyzer and through the bridge line, to force venous blood in the venous line toward the patient venous access and arterial blood in the arterial line toward the patient arterial access.

2. The dialysis system of claim 1, wherein the bridge line is coupled to the venous line at a venous line connection position and to the arterial line at an arterial line connection position and wherein the venous line downstream of the venous line connection and the arterial line upstream of the arterial line connection is approximately equal in length.

3. The dialysis system of claim 1, further comprising an air detector positioned in the venous line upstream of the bridge line.

4. The dialysis system of claim 1, wherein an interior of the bridge line defines a volume that is between about 0.3 ml and 0.7 ml.

5. The dialysis system of claim 1, wherein the bridge line has an inner diameter of 3.6 mm to 4.0 mm and a length of 80 mm to 100 mm.

6. The dialysis system of claim 1, further comprising:
a first clamp configured and positioned to selectively block and unblock the fluid source line;
a second clamp configured and positioned to selectively block and unblock the arterial line between the bridge line and the fluid port, and
a third clamp configured and positioned to selectively block and unblock the bridge line.

7. The dialysis system of claim 6, wherein the first clamp, the second clamp, and third clamp each include a selectively controllable electronic clamp and wherein the system further comprises:
a processor configured to control the selectively controllable electronic clamp of the first clamp, the second clamp, and the third clamp.

8. The dialysis system of claim 1, further comprising:
a first clamp configured and positioned to selectively block and unblock the fluid source line; and
a three-way valve positioned within the arterial line adjacent the bridge line, the three-way valve having a first port coupled to the bridge line, a second port coupled to an upstream portion of the arterial line and a third port coupled to a downstream portion of the arterial line.

9. The dialysis system of claim 8, wherein the three-way valve comprises:

an aseptic blood return configuration mode in which the first port is coupled to the second port and the third port is blocked;
a bridge line priming configuration mode in which the first port is coupled to the third port and the second port is blocked;
an arterial line priming configuration mode in which the first port is blocked and the second port is coupled to the third port;
a venous line priming configuration mode in which the first port is blocked and the second port is coupled to the third port; and
a therapy configuration mode in which the first port is blocked and the second port is coupled to the third port.

10. The dialysis system of claim 8, further comprising:
a processor configured to selectively control the three-way valve.

11. The dialysis system of claim 1, further comprising:
a memory configured to store program instructions; and
a processor coupled to the memory, the processor configured to processes the program instructions to configure the dialysis system to perform functions, including a function for:
configuring the dialysis system for priming the bridge line by blocking the arterial line between the bridge line and a patient, unblocking the arterial line between the bridge line and the fluid port, unblocking the bridge line, and unblocking the fluid source line.

12. The dialysis system of claim 1, further comprising:
a memory configured to store program instructions; and
a processor coupled to the memory, the processor configured to processes the program instructions to configure the dialysis system to perform functions, including a function for:
configuring the dialysis system for priming the arterial line by unblocking the arterial line between the bridge line and a patient, unblocking the arterial line between the bridge line and the fluid port, blocking the bridge line, and unblocking the fluid source line.

13. The dialysis system of claim 1, further comprising:
a memory configured to store program instructions; and
a processor coupled to the memory, the processor configured to processes the program instruction to configure the dialysis system to perform functions, including functions to:
configuring the dialysis system for priming the venous line by blocking the arterial line between the bridge line and a patient, unblocking the arterial line between the bridge line and the fluid port, blocking the bridge line, and unblocking the fluid source line:
operating the pump in a forward direction to produce fluid flow from the fluid source and through the dialyzer to force the fluid into the venous line toward the patient.

14. A fluid management method for use on a blood flow side of a dialysis system, the dialysis system comprising a fluid source, a dialyzer, a pump, a venous line fluidly coupled to a venous port of the dialyzer, an arterial line engaging the pump and fluidly coupled to an arterial port of the dialyzer on a first engagement side of the pump, a bridge line coupled between the venous line and the arterial line on a second engagement side of the pump, a fluid source line coupled between the fluid source and a fluid port of the arterial line on the second engagement side of the pump between the bridge line and the pump, a memory configured to store program instructions, and a processor coupled to the memory, the processor configured to process the program instructions to configure the dialysis system to perform steps of the method comprising:

configuring the dialysis system for aseptic blood return to a patient, when the patient is coupled to a patient venous access and a patient arterial access, by blocking the arterial line between the bridge line and the fluid port, unblocking the bridge line, and unblocking the fluid source line; and operating the pump in a forward direction to produce fluid flow from the fluid source, through the dialyzer, and through the bridge line to force venous blood in the venous line toward the patient venous access and arterial blood in the arterial line toward the patient arterial access.

15. The method of claim 14, further comprising the step of:

detecting air in the venous line; and stopping the pump in response to detecting air in the venous line.

16. The method of claim 14, further comprising the step of:

configuring the dialysis system for priming the bridge line by blocking the arterial line between the bridge line and the patient, unblocking the arterial line between the bridge line and the fluid port, unblocking the bridge line, and unblocking the fluid source line.

17. The method of claim 14, further comprising the step of:

configuring the dialysis system for priming the arterial line by unblocking the arterial line between the bridge line and the patient, unblocking the arterial line between the bridge line and the fluid port, blocking the bridge line, and unblocking the fluid source line.

18. The method of claim 14, further comprising the steps of:

configuring the dialysis system for priming the venous line by blocking the arterial line between the bridge line and the patient, unblocking the arterial line between the bridge line and the fluid port, blocking the bridge line, and unblocking the fluid source line:

operating the pump in a forward direction to produce fluid flow from the fluid source and through the dialyzer to force the fluid into the venous line toward the patient.

19. The method of claim 14, wherein the dialysis system further comprises a first clamp configured and positioned to selectively block and unblock the fluid source line, a second clamp configured and positioned to selectively block and unblock the arterial line between the bridge line and the fluid port, and a third clamp configured and positioned to selectively block and unblock the bridge line and wherein the configuring comprises:

selectively controlling the first clamp, the second clamp, and the third clamp.

\* \* \* \* \*